(12) United States Patent
Liu et al.

(10) Patent No.: US 12,059,677 B2
(45) Date of Patent: Aug. 13, 2024

(54) METHOD OF GENE SEQUENCING BASE ON SINGLE MOLECULE PCR LIBRARY PREPARATION ON A MICROWELL ARRAY CHIP

(71) Applicant: ZHANGJIAGANG ONE-CHIP BIOTECHNOLOGY CO., LTD., Jiangsu (CN)

(72) Inventors: Yabao Liu, Jiangsu (CN); Yaofei Yue, Jiangsu (CN); Zhifeng Zhang, Jiangsu (CN)

(73) Assignee: ZHANGJIAGANG ONE-CHIP BIOTECHNOLOGY CO., LTD., Suzhou (CN)

( * ) Notice: Subject to any disclaimer, the term of this patent is extended or adjusted under 35 U.S.C. 154(b) by 1010 days.

(21) Appl. No.: 16/971,967

(22) PCT Filed: Apr. 12, 2019

(86) PCT No.: PCT/CN2019/082561
§ 371 (c)(1),
(2) Date: Nov. 12, 2020

(87) PCT Pub. No.: WO2019/161810
PCT Pub. Date: Aug. 29, 2019

(65) Prior Publication Data
US 2021/0077995 A1 Mar. 18, 2021

(30) Foreign Application Priority Data
Feb. 22, 2018 (CN) .......................... 201810153345.9

(51) Int. Cl.
| C12Q 1/6806 | (2018.01) |
| B01L 3/00 | (2006.01) |
| C12N 15/10 | (2006.01) |
| C12Q 1/6874 | (2018.01) |

(52) U.S. Cl.
CPC ........ B01L 3/5027 (2013.01); C12N 15/1096 (2013.01); C12Q 1/6806 (2013.01); C12Q 1/6874 (2013.01); B01L 2300/0829 (2013.01)

(58) Field of Classification Search
CPC ............... B01L 3/5027; B01L 3/50851; B01L 2300/0829; B01L 2300/0663; C12N 15/1096; C12Q 1/6806; C12Q 1/6874; C12Q 1/6869
See application file for complete search history.

(56) References Cited

U.S. PATENT DOCUMENTS

| 6,556,940 B1 * | 4/2003 | Tretiakov .................. B01L 7/52 |
| | | 702/132 |
| 2006/0073491 A1 * | 4/2006 | Joseph .................. C12Q 1/6844 |
| | | 435/6.15 |
| 2016/0280723 A1 * | 9/2016 | Zhang .................... C07F 7/1876 |
| 2016/0333402 A1 * | 11/2016 | Koller ...................... C40B 40/06 |
| 2017/0321271 A1 * | 11/2017 | Hubbell ............... C12Q 1/6874 |

FOREIGN PATENT DOCUMENTS

| CN | 101128601 A | 2/2008 |
| CN | 101942513 A | 1/2011 |
| CN | 102203282 A | 9/2011 |
| CN | 102899244 A | 1/2013 |
| CN | 107460233 A | 12/2017 |
| WO | WO-2008076406 A2 * | 6/2008 ........... C12Q 1/6818 |

OTHER PUBLICATIONS

Ambardar et al., "High Throughput Sequencing: An Overview of Sequencing Chemistry," 2016, Indian Journal of Microbiology, vol. 56, Issue 4, pp. 394-404. (Year: 2016).*
Gharizadeh et al., "Type-Specific Multiple Sequencing Primers: A Novel Strategy for Reliable and Rapid Genotyping of Human Papillomaviruses by Pyrosequencing Technology," 2005, The Journal of Molecular Diagnostics, vol. 7, Issue 2, pp. 198-205. (Year: 2005).*
Bio-Rad Laboratories, "DNA Engine Thermal Cycler Operations Manual Version 4.0," 2005. (Year: 2005).*
Voelkerding et al., "Next-Generation Sequencing: From Basic Research to Diagnostics," 2009. Clinical Chemistry. vol. 55, Issue 4, pp. 641-658. (Year: 2009).*
Zhang et al., "A Microfluidic Liquid Phase Nucleic Acid Purification Chip to Selectively Isolate DNA or RNA from Low Copy/Single Bacterial Cells in Minute Sample Volume Followed by Direct On-Chip Quantitative PCR Assay," 2012. Analytical Chemistry. vol. 85. pp. 1484-1491. (Year: 2012).*
Mamanova et al., "Target-enrichment strategies for next-generation sequencing," 2010. Nature Methods. vol. 7. Issue 2. pp. 111-118. (Year: 2010).*
Mamanova et al., Supplemental Methods. 2010. 44 pages. (Year: 2010).*
Sakata et al., "Immobilization of oligonucleotide probes on Si3N4 surface and its application to genetic field effect transistor," 2004. Materials Science and Engineering C. vol. 24. pp. 827-832. (Year: 2004).*

(Continued)

*Primary Examiner* — Angela M. Bertagna
*Assistant Examiner* — Francesca Filippa Giammona
(74) *Attorney, Agent, or Firm* — Amanda M. Prose; Westman, Champlin & Koehler, P.A.

(57) ABSTRACT

Provided is a method of gene sequencing on a microwell array chip, including: Step 1: adding a PCR amplification system containing DNA fragments to be sequenced into the microwell array chip, allowing microwells to each individually form reaction spaces and allowing one DNA fragment to be contained in one microwell; Steps 2 to 3: subjecting the microwell array chip to PCR amplification, and denaturing amplified double-stranded DNAs in individual microwells; and Steps 4 and 5: sequencing the DNA fragments with sequencing primer S2 molecules and dNTPs in each microwell with a sensor at the bottom of the microwell.

8 Claims, 6 Drawing Sheets
Specification includes a Sequence Listing.

(56) References Cited

OTHER PUBLICATIONS

Office Action issued for Chinese patent application serial No. 201810153345.9, dated Mar. 19, 2021, with English translation.
International Search Report and Written Opinion issued for PCT/CN2019/082561, dated Sep. 2, 2019.
Mamonova, L. et al. "Target-Enrichment Strategies for Next-Generation Sequencing" Nature Methods, vol. 7, No. (2), Feb. 28, 2010, pp. 111-119.

* cited by examiner

Single molecule library is constructed and two terminals of DNA fragments to be tested are respectively ligated with A adaptor and P adaptor

A mixture solution of DNA fragments to be tested in combination with PCR amplification solution of DNA polymerase, deoxy-ribonucleoside triphosphates (dNTPs) and amplification primer A molecules is added into microwells of microwell array chip modified with oligonucleotide P1 molecules at inner surfaces

Microwell array chip is sealed by a sealing cover on its surface, such that microwells on the microwell array chip each individually form reaction spaces for PCR amplification reaction

Amplified DNA fragments are fixed at inner surfaces of microwells

Amplified double-stranded DNA molecules of DNA fragment in individual microwell are denatured to single-stranded DNA molecules by using NaOH solution. Single-stranded DNA molecules not paired with oligonucleotide P1 molecules are washed away

Incubating single-stranded DNA molecules, sequencing primer molecules and sequencing enzyme in microwells

Adding dNTPs into microwells in sequence of dGTP, dCTP, dATP and dTTP in one sequencing cycle for sequencing

dNTP paired with a base under sequencing releases hydrogen ion, resulting in signal response. Signal is converted into gene sequence information. DNA fragments to be tested are sequenced base-by-base to obtain whole gene sequence information

Figure 5

METHOD OF GENE SEQUENCING BASE ON SINGLE MOLECULE PCR LIBRARY PREPARATION ON A MICROWELL ARRAY CHIP

PRIORITY INFORMATION

This application is a US national phase application based upon PCT Application No. PCT/CN2019/082561 filed with the China National Intellectual Property Administration on Apr. 12, 2019, and claims priority to Chinese Patent Application No. 201810153345.9, filed on Feb. 22, 2018, the entire content of which is incorporated herein by reference.

FIELD

The present disclosure relates to a method of gene sequencing based on single molecule PCR library preparation on a microwell array chip, which belongs to the field of gene sequencing.

BACKGROUND

Obtaining genetic information of organisms quickly and accurately has always been of great significance for life science research. For each organism, genome carries whole genetic information of the organism. Thus, sequencing technology capable of accurately reflecting the genetic information on genome would comprehensively reveal the complexity and diversity of the genome, playing a very important role in life science research.

Sequencing technology can be traced back to the 1950s. As early as 1954, there were reports on early sequencing technology. For example, Whitfeld et al. obtained sequences of polyribonucleotides by chemical degradation method. The dideoxynucleotide chain termination method proposed by Sanger et al. (Sanger's method) and the chemical degradation method proposed by Gilbert et al. in 1977 marked the birth of first generation sequencing. Since then, second generation sequencing has been developed in the next thirty years, including 454 technology of Roche®, Solexa technology of Illumina® and SOLiD technology of ABI™ Recently, single molecule sequencing of Helicos™, single molecule real-time (SMRT) sequencing of Pacific Biosciences® and nanopore-based single molecule sequencing researched by Oxford Nanopore Technologies® have been taken as third-generation sequencing. Meanwhile, the second generation sequencing represented by Illumina® and the semiconductor-based gene sequencing by America's Ion Torrent™ have achieved breakthroughs, creating the next-generation sequencing (NGS). The next-generation sequencing allows high-throughput parallel sequencing via massive sensor arrays, greatly reducing the cost and time of sequencing and improving accuracy to 99% above. Sequencing technology is developing towards high-throughput, low-cost and high-accuracy.

However, current sequencing methods have many problems. For example, the first generation sequencing is cost-expensive, with estimated 3 billion dollars for the completion of the Human Genome Project. The first generation sequencing generates a huge amount of data to be analyzed, which is under low degree of automation and requires manual operations. Further, some polymerase chain reaction (PCR) products cannot be analyzed by the first generation sequencing, which needs the preparation of single-clones. Furthermore, the first generation sequencing is time-consuming, leading to a long sequencing time, with estimated at least 3 years for the completion of sequencing the human genome. For the second-generation sequencing, it still generates a relatively large workload and needs a high cost for patch processing of large number of samples, which is not cost effective for detection of small number of genes. More important, the second-generation sequencing is for relatively short reads, with a relatively slow sequencing speed and a large use amount of templates, thus cannot be useful in detection of a single cell or a single molecule. The third-generation sequencing is capable of detecting a whole genome with a low amount of initial material, high-throughput and high degree of automation, whereas it is not suitable for the detection of single gene locus with a relatively low requirement on sequencing, such as for genetic diagnosis of monogenic diseases, that is, resulting in a reduced cost performance. Further, the third-generation sequencing still has needs in reducing background noise, improving accuracy and decreasing sequencing cost. In addition, there is still need to prevent the generation of dimer structures while maintaining the extension performance of DNA molecules during fixing DNA molecules.

A next-generation sequencing technology, such as semiconductor-based sequencing technology of Ion Torrent™, adopted a semiconductor ion-sensitive field-effect sensor, with continually reduced sensor size and increased array scale by means of Moore's Law in the semiconductor industry, thus improving sequencing throughput and decreasing sequencing cost. However, Ion Torrent™ semiconductor-based sequencing technology is cumbersome in operation, including water-in-oil type microdrop/single molecule library DNA amplification reaction via the OneTouch2 device, magnetic bead purification and DNA denaturation via the ES device, DNA library sequencing on a chip via chip-centrifuge, which needs multiple sequencing-relative devices, causing a complicated sequencing process and a long sequencing time.

SUMMARY

Embodiments of the present disclosure aim at solving the problems or deficiencies existing in the related art. For this, the present disclosure in embodiments provides a method of gene sequencing based on a single molecule library preparation on a microwell array chip, the single molecule library being further amplified by PCR on the same microwell array chip, thus simplifying the complicated sequencing process, simplifying sequencing-relative devices, decreasing the use amount of reagents and reducing sequencing time and cost compared to the prior art.

In an aspect of the present disclosure, provided in embodiments is a method of gene sequencing based on a single molecule library preparation on a microwell array chip, the single molecule library being further amplified by PCR on the same microwell array chip, the method including:

Step 1: adding a mixture solution of DNA fragments to be tested in combination with a PCR amplification solution of DNA polymerase, deoxy-ribonucleoside triphosphates (dNTPs) and amplification primer S1 molecules into the microwell array chip, allowing each microwell on the microwell array chip to contain the mixture solution, and sealing the microwell array chip by a sealing cover on its surface, such that microwells on the microwell array chip each individually form reaction spaces, allowing one DNA fragment to be contained in one microwell, Step 2: subjecting the sealed microwell array chip after step 1 to PCR amplification reaction on a PCR machine, wherein the one DNA fragment is fixed at an inner surface of the one microwell after PCR amplification reaction, Step 3: removing the sealing cover and the solution in the microwell after the PCR amplification reaction in step 2,
  denaturing amplified double-stranded DNA molecules of the DNA fragment in individual microwell to single-stranded DNA molecules, and
  washing the microwells with a washing solution, followed by removing the washing solution, Step 4: adding a solution of sequencing primer S2 molecules into the microwells of the microwell array chip after step 3,
  subjecting the single-stranded DNA molecules of the DNA fragment in individual microwell and the sequencing primer S2 molecules to annealing, thus allowing the sequencing primer S2 molecules to be paired with the single-stranded DNA molecules,
  discarding the remaining solution in microwells, followed by adding a solution of sequencing enzyme, and
  incubating the single-stranded DNA molecules paired with the sequencing primer S2 molecules and the solution of sequencing enzyme, Step 5: adding dNTPs into the microwells in sequence of dGTP, dCTP, dATP and dTTP for sequencing,
  wherein the dNTP capable of pairing with a base under sequencing of the single-stranded DNA molecule as a template is ligated to the 3' terminal of the sequencing primer S2 molecule in the presence of the sequencing enzyme, with hydrogen ions or pyrophosphate PPi ions released, and thus charges of DNA backbones increased,
  the released hydrogen ions or pyrophosphate PPi ions or increased charges of DNA backbones result in signal response of a sensor at bottom of the microwell,
  the signal by the sensor is recorded and converted into gene sequence information of the DNA fragments to be tested, and Step 6: repeating step 5 for sequencing the DNA fragments to be tested base-by-base in microwells,
  wherein the one DNA fragment is fixed at an inner surface of the one microwell by
  modifying inner surfaces of the microwells with oligonucleotide L1 molecules and ligating an S adaptor and an L adaptor to two terminals of the DNA fragments to be tested respectively before the step 1, such that the L adaptor of the DNA fragment to be tested is paired with the oligonucleotide L1 molecule at the inner surface of the microwell via annealing during the step 2, thereby fixing the DNA fragments to be tested at the inner surfaces of the microwells.

According to embodiments of the present disclosure, the method may further include at least one of the following additional technical features.

In embodiments of the present disclosure, the microwell array chip includes:
  a semiconductor chip with a plurality of microwells on its surface, wherein an inner surface of the microwell is fixed with an oligonucleotide L1 molecule layer via chemical modification, and
  a sensor located at the bottom of the microwell, wherein the sensor includes an ion sensitive field effect sensor or a nanowire transistor sensor.

In embodiments of the present disclosure, the released hydrogen ions or pyrophosphate PPi ions or increased charges of DNA backbones during base extension trigger a current or voltage change of the sensor located at the bottom of the microwell, thus converting a chemical signal into an electrical signal, and
  the electrical signal is further converted into corresponding gene sequence information.

In embodiments of the present disclosure, the microwell array chip further includes a device for PCR amplification reaction,
  wherein the device for PCR amplification reaction includes a base support adapted for a PCR heating nest or a PCR heating plate, the sealing cover for the microwell and a lid,
  wherein the base support is provided with a chip holder to accommodate the microwell array chip,
  the lid is provided with a buckle, and
  the base support, the chip holder, the sealing cover and the lid are center horizontally aligned.

In embodiments of the present disclosure, a surface of the sensor is coated with a layer of probes selective for pyrophosphate PPi ions or phosphate ions, or a thin film allowing selective penetration of the pyrophosphate PPi ions or phosphate ions.

In embodiments of the present disclosure, the annealing in step 4 is performed by: subjecting the microwell array chip in the PCR machine to being at 80 to 99° C. for 0.5 to 10 minutes and then at 15 to 55° C. for 0.5 to 10 minutes, so as to allow the sequencing primer S2 molecules to be paired with the single-stranded DNA molecules of the DNA fragment fixed in individual microwell,
  discarding the remaining solution in microwells, followed by adding a solution of sequencing enzyme, and
  incubating the single-stranded DNA molecules paired with the sequencing primer S2 molecules and the solution of sequencing enzyme at 20 to 40° C. for 0.5 to 30 minutes before sequencing.

In embodiments of the present disclosure, discarding the remaining solution in microwells is performed by using vacuum pumping, microfluidic flushing with cleaning fluid, or gas blowing.

In embodiments of the present disclosure, modifying inner surfaces of the microwells with oligonucleotide L1 molecules is performed by:
  1) allowing a semiconductor chip with a plurality of microwells on its surface to be in an organic solution containing amino molecules for amination modification, such that the inner surfaces of the microwells are provided with an amino structure,
  2) subjecting the amination modified semiconductor chip to being reacted with a glutaraldehyde solution under the catalyzation of sodium cyanoborohydride, thus allowing a polymerization reaction between amino groups on the inner surfaces of the microwells and aldehyde groups of the glutaraldehyde, such that the inner surfaces of the microwells in the semiconductor chip are modified with aldehyde groups,
  3) modifying the 5' terminal of the oligonucleotide L1 molecules with amino groups, and
  4) subjecting the aldehyde groups on the inner surfaces of the microwells and the amino groups modified at the 5' terminal of the oligonucleotide L1 molecules to a polymerization reaction under the catalyzation of sodium cyanoborohydride, so as to allow coupling the oligonucleotide L1 molecules to the microwells of the semiconductor chip.

In embodiments of the present disclosure, the amino molecules are amino-propyltrioxyethyl silane (APTES) or N-(2-aminoethyl)-3'-aminopropyl triethoxysilane (AEAPTES), and the amination modification is performed by a vapor deposition process so as to form a dense monolayer on the inner surface of the microwell.

In embodiments of the present disclosure, the electrical signal is further converted into corresponding gene sequence information by:
1) collecting data of an original electrical signal matrix generated after respective addition of dGTP, dCTP, dATP and dTTP in sequence, thus obtaining four original electrical signal matrices in a sequencing cycle,
2) classifying the original electrical signal matrices respectively to generate four classified data matrices, followed by deleting the original electrical signal matrices,
3) determining gene types of the DNA fragments to be tested in individual microwells in the sequencing cycle according to the four classified data matrices, and generating a DNA base information matrix, and
4) connecting all DNA base information matrices obtained from beginning to end in sequence to form a DNA matrix sequence.

The present disclosure in embodiments achieved the following beneficial technical effects.
1) The present disclosure achieves single molecule library DNA amplification reaction and subsequent sequencing on a single semiconductor chip microarray, thus avoiding single molecule library DNA amplification reaction on water-in-oil type microdrops via the OneTouch2 device, magnetic bead purification and DNA denaturation via the ES device, DNA library sequencing on a chip via chip-centrifuge compared to the prior art, thereby greatly simplifying the sequencing process, shortening the sequencing time and reducing the sequencing cost.
2) The present disclosure simplified the sequencing process and saved corresponding supporting reagents, thus reducing the sequencing cost.
3) The present disclosure provided a reaction system based on individually independent microwells, reducing the use amount of sequencing reagents compared to the prior art, thus saving the cost caused by PCR amplification reaction and sequencing.

BRIEF DESCRIPTION OF THE DRAWINGS

FIG. 5 is a flowchart of a method of gene sequencing based on a single molecule PCR library on a microwell array chip according to an embodiment of the present disclosure.

Figure 1:
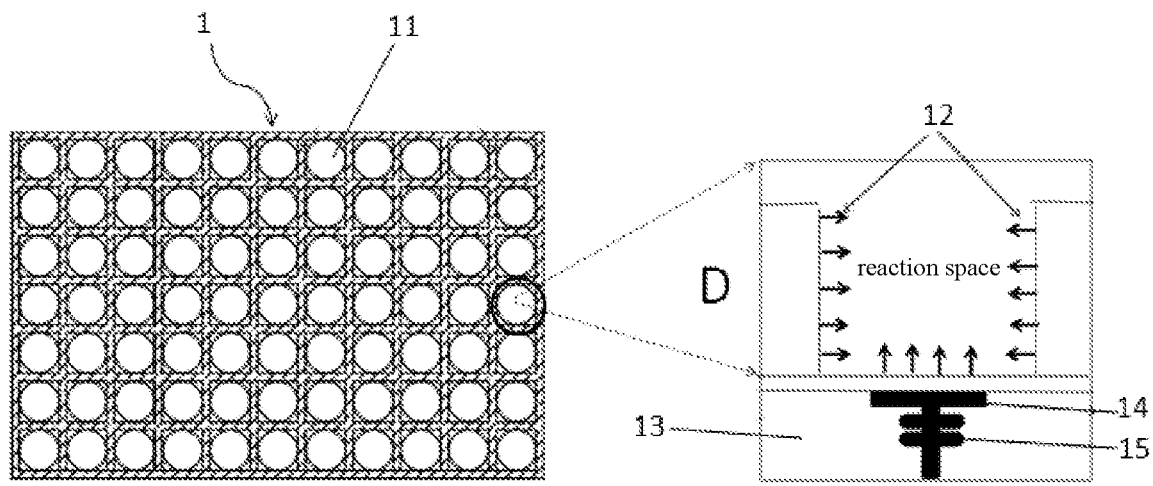
FIG. 1 is a schematic diagram of the structure of microwell arrays of a semiconductor chip according to an embodiment of the present disclosure, in which "D" represents an enlarged schematic diagram of the structure of microwells.

In which, semiconductor chip body 1; microwell 11; oligonucleotide L1 molecule layer 12; foundation 13; sensor 14; metal layer 15; primer S1 molecules 2; DNA fragments to be tested 3; sealing plate 4; primer S2 molecules 5; 96-well plate 6; device for PCR amplification reaction 7; base support 71; chip holder 72; lid 73; sealing cover 74; buckle 75.

DETAILED DESCRIPTION

The present disclosure will be further described below in combination with specific embodiments. The following embodiments are only used to illustrate the technical solutions of the present disclosure clearly and cannot be construed to limit the scope of the present disclosure.

The technical solutions of the present disclosure are specifically described in combination of drawings and embodiments.

Referring to FIG. 5, the present disclosure in embodiments provides a method of gene sequencing based on a single molecule library preparation on a microwell array chip, the single molecule library being further amplified by PCR on the same microwell array chip, in which the method specifically includes the following steps.

Step 1: A solution of DNA fragments to be tested in a concentration of 1 to 100 pmol/L was mixed with a PCR amplification solution of DNA polymerase, deoxy-ribonucleoside triphosphates (dNTPs) and amplification primer S1 molecules thoroughly. The amplification primer S1 molecule is of a nucleotide sequence of 5'-CCATCT-CATCCCTGCGTGTCTC-3' (SEQ ID NO: 2).

The mixture solution was added into a microwell array chip, allowing each microwell on the microwell array chip to contain the mixture solution, in which the mixture solution was adjusted to contain DNA fragments with a number not more than the number of microwells on the microwell array chip, such that only one DNA fragment was contained in one microwell mostly whereas there might be zero or more than one DNA fragment in a small portion of microwells. After that, the microwell array chip was covered with and tightly sealed by a sealing cover or a flexible film on the surface, such that microwells on the microwell array chip each individually form reaction spaces, thus allowing as many microwells as possible to be each independently contained and only contained with one DNA fragment.

In a specific embodiment, the DNA fragment to be tested is of a nucleotide sequence of 5'-CCATCT-CATCCCTGCGTGTCTCCGACTCAG(NNNNNN NNNN)$_{(1-40)}$TCACCGACTGC CCATAGAGAGG-3' (SEQ ID NO: 4).

Step 2: The sealed microwell array chip obtained after step 1 was subjected to PCR amplification reaction on a PCR machine.

Figure 3:
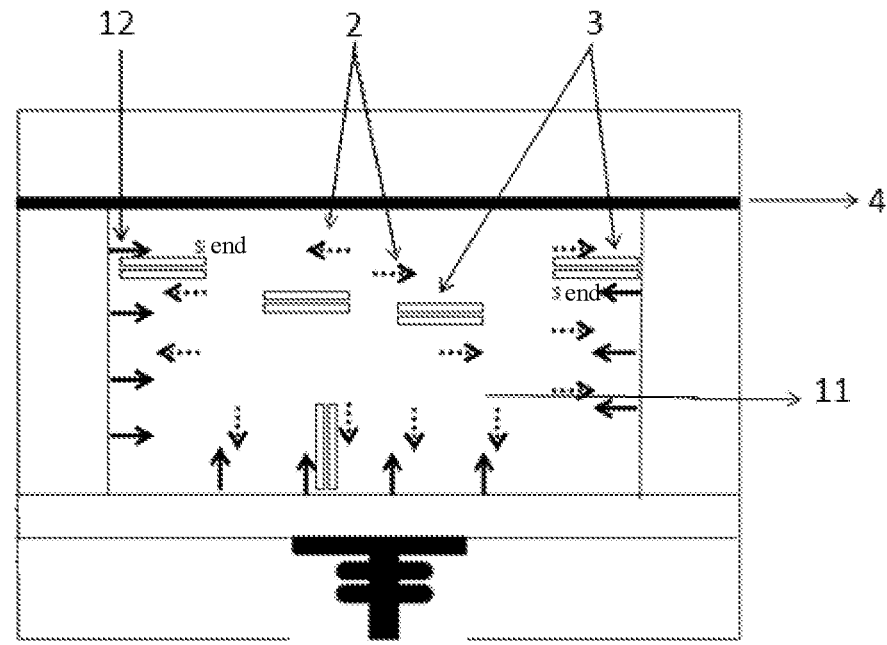
FIG. 3 is a schematic diagram of PCR amplification reaction of DNA fragments to be tested in microwells of a microwell array chip according to an embodiment of the present disclosure.

Referring to FIG. 3, the semiconductor chip may be arranged on a flat-plate PCR machine directly during the PCR amplification reaction. The semiconductor chip may be arranged on a traditional PCR machine by means of a device for PCR amplification reaction during the PCR amplification reaction, for example, the semiconductor chip is a 96-well plate. During the PCR amplification reaction, one or more devices for PCR amplification reaction uniquely adapted to be matched with the 96-well plate were inserted into wells of the 96-well plate. The device for PCR amplification reaction is provided with a base support made of metal or other thermally conductive materials to allow heating the semiconductor chip. The semiconductor chip may be heated or cooled via the sealing plate on the surface of the semiconductor chip, so as to ensure the performance of PCR amplification reaction. The conditions for the PCR amplification reaction are shown in Table 1.

TABLE 1

PCR amplification conditions

|        | Temperature | Time | Cycle |
|--------|-------------|------|-------|
| Step 1 | 95° C. | 3 minutes | 1 cycle |
| Step 2 | 95° C. | 30 seconds | 30 to 40 cycles |
| Step 3 | decrease from 95° C. to 56° C. at a rate of 1° C./0.2 seconds | | |
| Step 4 | 56° C. | 30 seconds | |
| Step 5 | increase from 56° C. to 72° C. at a rate of 1° C./0.2 seconds | | |
| Step 6 | 72° C. | 45 seconds | |
| Step 7 | 72° C. | 10 minutes | 1 cycle |
| Step 8 | 25° C. | — | |

Step 3: The sealing cover on the surface of the semiconductor chip and the solution in the microwell were removed after the PCR amplification reaction in step 2, after that amplified double-stranded DNA molecules of the DNA fragment in individual microwell were denatured to single-stranded DNA molecules by using alkaline solutions such as NaOH solution or KOH solution or other available methods. Subsequently, the solution in the microwell was removed and the microwells were further washed with a washing solution, followed by removing the washing solution.

Step 4: A solution of sequencing primer S2 molecules was added into the microwells of the microwell array chip after step 3, in which the sequencing primer S2 molecule is of a nucleotide sequence of 5'-CCATCT-CATCCCTGCGTGTCTCCGAC-3' (SEQ ID NO: 3).

Figure 4:
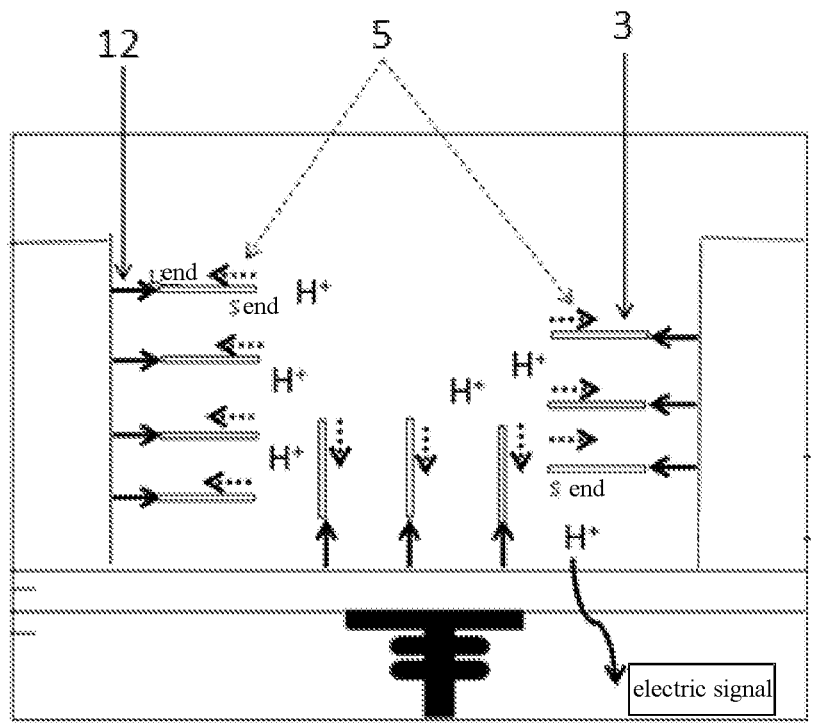
FIG. 4 is a schematic diagram of sequencing DNA fragments to be tested in microwells of a microwell array chip according to an embodiment of the present disclosure.

Referring to FIG. 4, the single-stranded DNA molecules of the DNA fragment in individual microwell and the sequencing primer S2 molecules were subjected to annealing after the microwell array chip was sealed by a sealing cover on its surface, thus allowing the sequencing primer S2 molecules to be paired with the single-stranded DNA molecules.

The annealing was performed by subjecting the sealed microwell array chip in a flat-plate PCR machine to being at 80 to 99° C. for 0.5 to 10 minutes and then at 15 to 55° C. for 0.5 to 10 minutes. Alternatively, the microwell array chip is a 96-well plate and the device for PCR amplification reaction uniquely adapted to be matched with the 96-well plate was used for performing the annealing on a traditional PCR machine according to a procedure of 80 to 99° C. for 0.5 to 10 minutes and then at 15 to 55° C. for 0.5 to 10 minutes. After the completion of annealing, the remaining solution in microwells was discarded, followed by adding a solution of sequencing enzyme and incubating the single-stranded DNA molecules paired with the sequencing primer S2 molecules and the solution of sequencing enzyme at 20 to 40° C. for 0.5 to 30 minutes before sequencing.

Step 5: dNTPs were added into the microwells in sequence of dGTP, dCTP, dATP and dTTP for sequencing, in which the dNTP capable of pairing with a base under sequencing of the single-stranded DNA molecule as a template was ligated to the 3' terminal of the sequencing primer S2 molecule in the presence of the sequencing enzyme, with hydrogen ions and pyrophosphate PPi ions released.

If the added dNTP was exactly paired with the base under sequencing of the single-stranded DNA molecule as a template, the added dNTP was ligated to the 3' terminal of the sequencing primer S2 molecule in the presence of the sequencing enzyme, thus releasing one hydrogen ion and one pyrophosphate PPi ion. If the added dNTP cannot be paired with the base under sequencing of the single-stranded DNA molecule as a template, the added dNTP would not be ligated to the 3' terminal of the sequencing primer S2 molecule in the presence of the sequencing enzyme, without hydrogen ions or pyrophosphate PPi ions released. If the added dNTP was not paired with the base under sequencing, another dNTP was added in sequence of dGTP, dCTP, dATP and dTTP until the base under sequencing paired to corresponding dNTP, with the hydrogen ion and the pyrophosphate PPi ion released. The released hydrogen ions or pyrophosphate PPi ions or increased charges of DNA backbones resulted in signal response of a sensor at bottom of the microwell. The signal generated by the sensor was recorded by a processor and then converted into gene sequence information of the DNA fragments to be tested.

Figure 6:
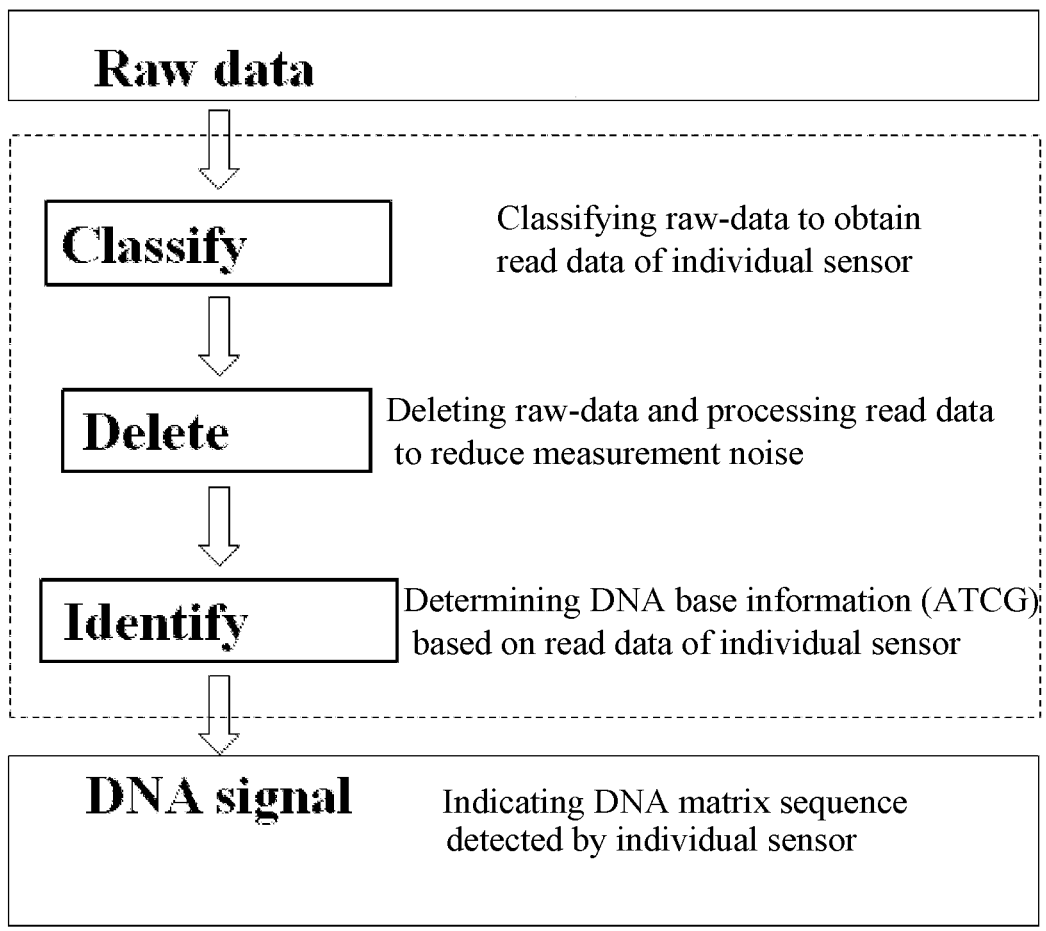
FIG. 6 is a flowchart of conversion of an electrical signal into gene sequence information of DNA fragments to be tested according to an embodiment of the present disclosure.

Referring to FIG. 6, the signal response of the sensor is a current or voltage change of the sensor. The electrical signal was further converted into corresponding gene sequence information by the following steps.

Figure 7:
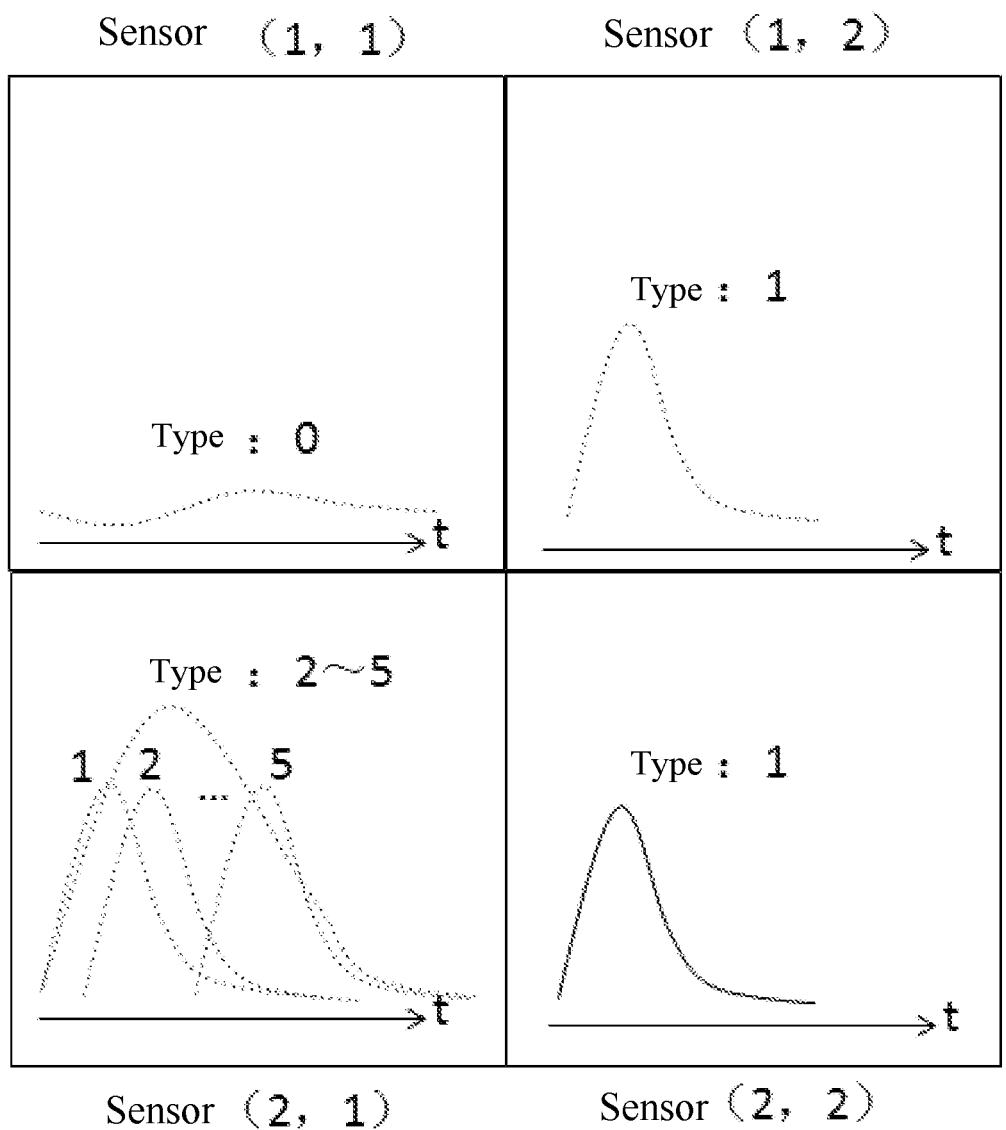
FIG. 7 is a schematic diagram of conversion of analog signals of DNA fragments to be tested in microwells into electrical signals according to an embodiment of the present disclosure.

1) Data of an original electrical signal matrix generated after respective addition of dGTP, dCTP, dATP and dTTP in sequence was collected, thus obtaining four original electrical signal matrices in a sequencing cycle. Referring to FIG. 7, taken 2×2 four sensors as an example, the original data is data points sampled 25 to 60 times per second, such that analog signals of DNA fragments to be tested in microwells were converted into digital signals, that is, electrical signals.

2) The original electrical signal matrices were classified respectively to generate four classified data matrices, followed by deleting the original electrical signal matrices to save the memory space. Referring to FIG. 7, specific bases of the DNA fragment to be tested being detected according to the change of pH value, the original electrical signal matrices can be classified to the following types: (1) Type: 0, no pulse signal received, indicating no signal response of the sensor caused by ligation reaction, and thus no dNTP paired to the base under sequencing; (2) Type: 1, one pulse signal of hydrogen ion received, indicating one dNTP paired to one base under sequencing; (3) Type: 2 to 5, two or more than two pulse signals of hydrogen ions received, indicating two or more than two dNTPs paired to two or more than two bases under sequencing, that is, multiple bases being sequenced.

Figure 8:
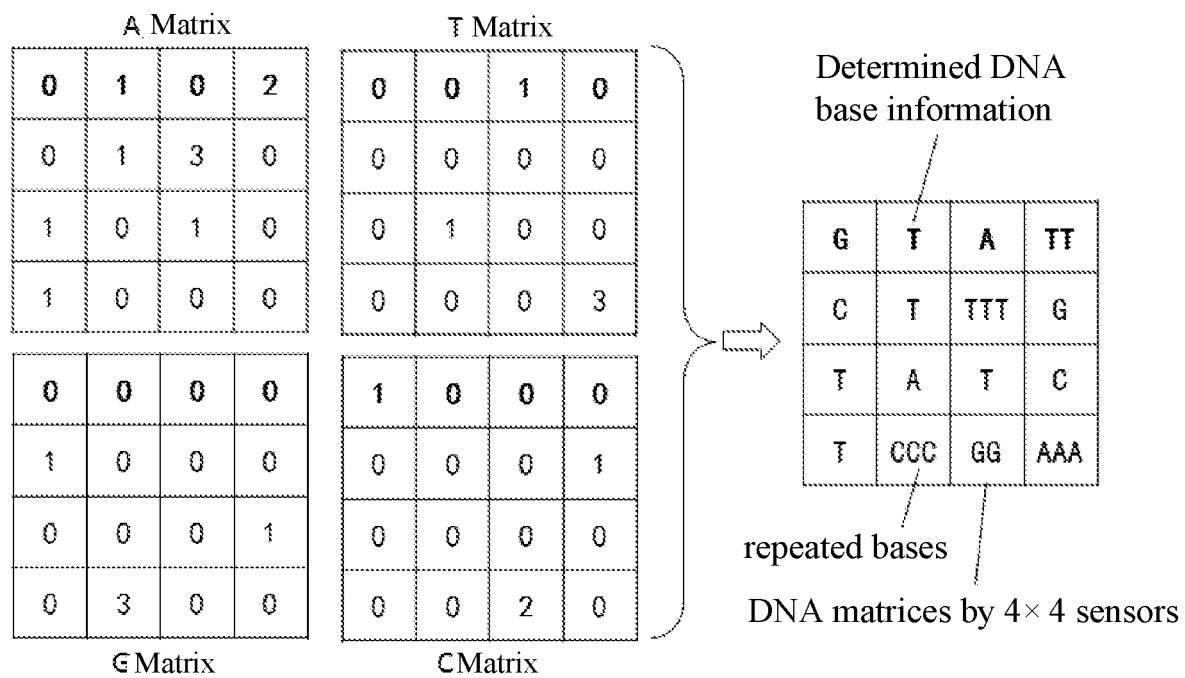
FIG. 8 is a schematic diagram of conversion of treated electrical signals into corresponding gene sequence information according to an embodiment of the present disclosure.

Referring to FIG. 8, four classified data matrices respectively corresponding to dGTP, dCTP, dATP and dTTP were produced. After that, the original electrical signal matrices were deleted to save the memory space. After this procedure, a primary analysis of data of original electrical signal matrices was completed and the data size was greatly reduced.

3) Gene types of the DNA fragments to be tested in individual microwells in one sequencing cycle were determined according to the four classified data matrices, and a DNA base information matrix was generated. Referring to FIG. 8, matrices A, T and G are all 0 and matrix C is 1 at the location (1, 1), indicating that the base corresponded to the location (1, 1) is base G paired to the base C. Similarly, matrices A, T and C are all 0 and matrix G is 3 at the location (2, 4), indicating that three bases C (i.e., CCC) corresponded to the location (2, 4). Thus, a DNA base information matrix was generated as an output after this procedure. Then, the DNA base information matrix obtained in this sequencing cycle followed the DNA base information matrix obtained in a previous sequencing cycle, producing a preliminary DNA matrix sequence.

4) All DNA base information matrices obtained from beginning to end in sequence were connected, thus forming a final DNA matrix sequence.

During the sequencing, current or voltage signal was generated by the sensor according to the following principles.

1) One pyrophosphate PPi ion generated during base extension can be hydrolyzed to two phosphate ions via hydrolysis reaction. Based on that, the surface of the sensor is coated with a layer of probes selective for pyrophosphate PPi ions or phosphate ions, or a thin film allowing selective penetration of the pyrophosphate PPi ions or phosphate ions. Thus, a voltage change can be generated by the Nernstein phenomenon. Further, the charge carried by one pyrophosphate PPi ion is four folds of the charge of one hydrogen ion, resulting in a slower diffusion rate, and a stronger and more stable signal.

2) The charges of base pairs of DNA molecules generated during a sequencing cycle can be constantly recorded, generating a direct-current signal, therefore the increased charges of DNA backbones generated during sequencing base-by-base are recorded to be step-like direct-current electrical signal.

3) The charges of base pairs of DNA molecules, and the released hydrogen ions or phosphate ions would generate different signals respectively during sequencing. Specifically, the increased charges of DNA backbones would generate a step-like direct-current electrical signal, whereas the released hydrogen ions or phosphate ions would generate a pulse signal. The hydrogen ions or phosphate ions are diffused out of the microwells with time. In practice, the effective pairing of added dNTP to the base under sequencing is determined by detection of both the step-like direct-current electrical signal and the pulse signal, thereby reducing the error rate of interferences generated during the sequencing, and improving data quality and sequencing accuracy.

Step 6: Step 5 was repeated for sequencing the DNA fragments to be tested base-by-base in microwells.

In the steps as described above, the solution in microwells is discarded by using (1) vacuum pumping, (2) microfluidic flushing with cleaning fluid, or (3) gas blowing, thus cleaning the microwells.

The sensor as described above includes an ion sensitive field effect sensor or a nanowire transistor sensor.

The addition of a solution as described above is performed by using a droplet addition method such as a droplet sequencer, or using a droplet control method such as an automatic pipette, an ink jet method and the like, thus reducing the use amount of solution.

Referring to FIG. 1, the microwell array chip used in the method as described above includes a semiconductor chip with a plurality of microwells on its surface, and a sensor located at the bottom of the microwell. The sensor includes an ion sensitive field effect sensor or a nanowire transistor sensor.

For the semiconductor chip with a plurality of microwells, an inner surface of the microwell is fixed with an oligonucleotide L1 molecule layer through chemical modification. The DNA fragments to be tested were ligated with an S adaptor and an L adaptor at two terminals respectively before the step 1, such that L adaptor of the DNA fragment to be tested is paired with the oligonucleotide L1 molecule at the inner surface of the microwell via annealing during the step 2, thereby fixing the DNA fragments to be tested at the inner surfaces of the microwells. After the PCR amplification system was added into microwells, the microwell array chip was covered with and tightly sealed by a sealing cover or a flexible film on the surface.

Figure 2:
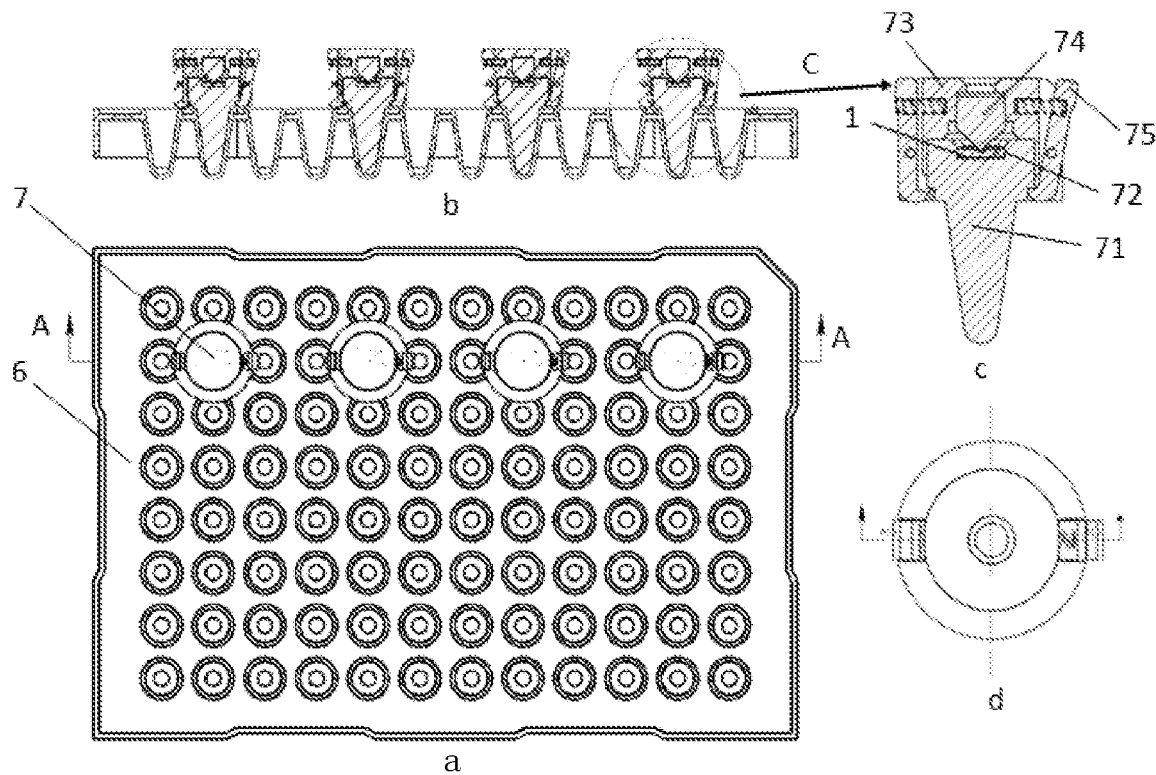
FIG. 2 is a schematic diagram of the structure of a device for PCR amplification reaction according to an embodiment of the present disclosure, in which "a" represents a schematic diagram of the structure of a 96-well plate adapted for PCR amplification reaction, "b" represents a schematic cross-sectional view along line A-A in the "a", "c" represents a schematic diagram of the structure of an enlarged "C" in the "b", and "d" represents a schematic diagram of the structure of a device for PCR amplification reaction.

The semiconductor chip may be arranged on a flat-plate PCR machine directly during the PCR amplification reaction. The semiconductor chip may be arranged on a traditional PCR machine by means of a device for PCR amplification reaction during the PCR amplification reaction, for example, the semiconductor chip is a 96-well plate. Referring to FIG. 2, the device for PCR amplification reaction includes a base support adapted for a PCR heating nest, a sealing cover for microwell and a lid. The base support is provided with a chip holder to accommodate the microwell array chip. The base support, the chip holder, the sealing cover and the lid are center horizontally aligned. The cover is provided with a buckle. During the PCR amplification reaction, one or more devices for PCR amplification reaction uniquely adapted to be matched with the 96-well plate were inserted into wells of the 96-well plate. The device for PCR amplification reaction is provided with the base support made of metal or other thermally conductive materials to allow heating the semiconductor chip. The semiconductor chip may be heated or cooled via the sealing plate on the surface of the semiconductor chip, so as to ensure the performance of PCR amplification reaction.

One pyrophosphate PPi ion generated during base extension can be hydrolyzed to two phosphate ions via hydrolysis reaction. Thus, in order to convert the pyrophosphate PPi ion signal into an electrical signal, the surface of the sensor may be coated with a layer of probes selective for pyrophosphate PPi ions or phosphate ions, or a thin film allowing selective penetration of the pyrophosphate PPi ions or phosphate ions. Thus, a voltage change can be generated by the Nernstein phenomenon.

According to the present microwell array chip, the inner surfaces of microwells of the semiconductor chip are fixed with an oligonucleotide L1 molecule layer through chemical modification. The chemical modification was performed as follows.

1.1) A semiconductor chip with a plurality of microwells on its surface was allowed to be in an alcohol solution containing amino molecules for amination modification, such that the inner surfaces of the microwells of the semiconductor chip are provided with an amino structure. The amino molecules are amino-propyltri-oxyethyl silane (APTES) or N-(2-aminoethyl)-3-aminopropyl triethoxysilane (AEAPTES). The APTES is treated by a vapor deposition process so as to form a dense monolayer on the inner surface of the microwell.

1.2) The amination modified semiconductor chip was subjected to being reacted with a glutaraldehyde solution under the catalyzation of sodium cyanoborohydride, thus allowing a polymerization reaction between amino groups on the inner surfaces of the microwells and aldehyde groups of the glutaraldehyde, such that the inner surfaces of the microwells in the semiconductor chip were modified with aldehyde groups.

1.3) The 5' terminal of the oligonucleotide L1 molecules was modified with amino groups. The oligonucleotide L1 molecule is of a nucleotide sequence of 5'-NH2-CCTCTCTATGGGCAGTCGGTGA-3' (SEQ ID NO: 1).

1.4) The aldehyde groups on the inner surfaces of the microwells and the amino groups modified at the 5' terminal of the oligonucleotide L1 molecules were subjected to a polymerization reaction under the catalyzation of sodium cyanoborohydride, so as to allow coupling the oligonucleotide L1 molecules to the microwells of the semiconductor chip.

The above preferred embodiments described the present disclosure, but are not intended to limit the present disclosure. Other technical solutions obtained by using equivalent substitutions or equivalent changes fall within the protection scope of the present disclosure.

What is claimed is:

1. A method of gene sequencing based on a single molecule library preparation on a microwell array chip, the single molecule library being further amplified by PCR on the same microwell array chip, the method comprising:

Step 1: adding a mixture solution of DNA fragments to be sequenced in combination with a PCR amplification solution of DNA polymerase, deoxy-ribonucleoside triphosphates (dNTPs) and amplification primer S1 molecules into the microwell array chip, allowing each microwell on the microwell array chip to contain the mixture solution, and sealing the microwell array chip by a sealing cover on its surface, such that the microwells on the microwell array chip each individually form reaction spaces, allowing one DNA fragment to be contained in one microwell, Step 2: subjecting the sealed microwell array chip after step 1 to PCR amplification on a PCR machine, wherein the one DNA fragment and amplified DNA fragments are fixed at an inner surface of the one microwell after PCR amplification, Step 3: removing the sealing cover and the solution in the microwell after the PCR amplification in step 2, denaturing amplified double-stranded DNA molecules of the DNA fragments in individual microwells to single-stranded DNA molecules, and washing the microwells with a washing solution, followed by removing the washing solution, Step 4: adding a solution of sequencing primer S2 molecules into the microwells of the microwell array chip after step 3, subjecting the single-stranded DNA molecules of the DNA fragments in individual microwells and the sequencing primer S2 molecules to annealing, thus allowing the sequencing primer S2 molecules to be paired with the single-stranded DNA molecules, discarding the remaining solution in the microwells, followed by adding a solution of sequencing enzyme, and incubating the single-stranded DNA molecules paired with the sequencing primer S2 molecules and the solution of sequencing enzyme, Step 5: adding dNTPs into the microwells in a sequence of dGTP, dCTP, dATP and dTTP for sequencing, wherein the dNTP capable of pairing wi-th a base under sequencing of the single-stranded DNA molecule as a template is ligated to the 3' terminal of the sequencing primer S2 molecule in the presence of the sequencing enzyme, with hydrogen ions or pyrophosphate PPi ions released, and thus charges of DNA backbones increased, the released hydrogen ions or pyrophosphate PPi ions or increased charges of DNA backbones result in a signal response from individual sensors at the bottom of each microwell, triggering a current or voltage change of the sensor, thus converting a chemical signal into an electrical signal;

the electrical signals by the sensors are recorded and converted into gene sequence information of the DNA fragments to be sequenced, and Step 6: repeating step 5 for sequencing the DNA fragments to be sequenced base-by-base in the microwells, wherein the one DNA fragment is fixed at an inner surface of the one microwell by modifying inner surfaces of the microwells with oligonucleotide L1 molecules and ligating an S adaptor and an L adaptor to two terminals of the DNA fragments to be sequenced respectively before step 1, such that the L adaptor of the DNA fragment to be sequenced is paired with the oligonucleotide L1 molecule at the inner surface of the microwell via annealing during step 2, thereby fixing the DNA fragments to be sequenced at the inner surfaces of the microwells, wherein in step 5, the electrical signal is further converted into corresponding gene sequence information by:

i) collecting data of an original electrical signal matrix generated after respective addition of dGTP, dCTP, dATP and dTTP in sequence, thus obtaining four original electrical signal matrices in a sequencing cycle, ii) classifying the original electrical signal matrices respectively to generate four classified data matrices, followed by deleting the original electrical signal matrices, iii) determining gene types of the DNA fragments to be sequenced in individual microwells in the sequencing cycle according to the four classified data matrices, and generating a DNA base information matrix, and iv) connecting all DNA base information matrices obtained from beginning to end in sequence to form a DNA matrix sequence.

2. The method according to claim 1, wherein the microwell array chip comprises:

a semiconductor chip with a plurality of microwells on its surface, wherein an inner surface of each microwell is fixed with an oligonucleotide L1 molecule layer via chemical modification, and a sensor located at the bottom of each microwell, wherein the sensor comprises an ion sensitive field effect sensor or a nanowire transistor sensor.

3. The method according to claim 2, wherein the microwell array chip further comprises a device for PCR amplification, wherein the device for PCR amplification comprises a base support adapted for a PCR heating nest or a PCR heating plate, the sealing cover for the microwell and a lid, wherein the base support is provided with a chip holder to accommodate the microwell array chip, the lid is provided with a buckle, and the base support, the chip holder, the sealing cover and the lid are center horizontally aligned.

4. The method according to claim 2, wherein a surface of the sensor is coated with a layer of probes selective for pyrophosphate PPi ions or phosphate ions, or a thin film allowing selective penetration of the pyrophosphate PPi ions or phosphate ions.

5. The method according to claim 1, wherein the annealing in step 4 is performed by:
  subjecting the microwell array chip in the PCR machine to being at 80 to 99° C. for 0.5 to 10 minutes and then at 15 to 55° C. for 0.5 to 10 minutes, so as to allow the sequencing primer S2 molecules to be paired with the single-stranded DNA molecules of the DNA fragments fixed in individual microwells,
  discarding the remaining solution in the microwells, followed by adding a solution of sequencing enzyme, and
  incubating the single-stranded DNA molecules paired with the sequencing primer S2 molecules and the solution of sequencing enzyme at 20 to 40° C. for 0.5 to 30 minutes before sequencing.

6. The method according to claim 1, wherein discarding the remaining solution in the microwells is performed by using vacuum pumping, microfluidic flushing with cleaning fluid, or gas blowing.

7. The method according to claim 1, wherein modifying inner surfaces of the microwells with oligonucleotide L1 molecules is performed by
  1) allowing a semiconductor chip with a plurality of the microwells on its surface to be in an organic solution containing amino molecules for amination modification, such that the inner surfaces of the microwells are provided with amino structures,
  2) subjecting the amination modified semiconductor chip to being reacted with a glutaraldehyde solution under the catalyzation of sodium cyanoborohydride, thus allowing a polymerization reaction between amino groups on the inner surfaces of the microwells and aldehyde groups of the glutaraldehyde, such that the inner surfaces of the microwells in the semiconductor chip are modified with aldehyde groups,
  3) modifying the 5' terminal of the oligonucleotide L1 molecules with amino groups, and
  4) subjecting the aldehyde groups on the inner surfaces of the microwells and the amino groups modified at the 5' terminal of the oligonucleotide L1 molecules to a polymerization reaction under the catalyzation of sodium cyanoborohydride, so as to allow coupling the oligonucleotide L1 molecules to the microwells of the semiconductor chip.

8. The method according to claim 7, wherein the amino molecules are amino-propyltrioxyethyl silane (APTES) or N-(2-aminoethyl)-3-aminopropyl triethoxysilane (AEAPTES), and
  the amination modification is performed by a vapor deposition process so as to form a dense monolayer on the inner surface of the microwell.

\* \* \* \* \*

```
                        SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: oligonucleotide L1 molecule
<220> FEATURE:
<221> NAME/KEY: modified_base
<222> LOCATION: (1)..(1)
<223> OTHER INFORMATION: amination modification

<400> SEQUENCE: 1
cctctctatg ggcagtcggt ga                                              22

<210> SEQ ID NO 2
<211> LENGTH: 22
<212> TYPE: DNA
<213> ORGANISM: Artificial Sequence
<220> FEATURE:
<223> OTHER INFORMATION: amplification primer S1 molecule

<400> SEQUENCE: 2
ccatctcatc cctgcgtgtc tc                                              22

<210> SEQ ID NO 3
<211> LENGTH: 26
<212> TYPE: DNA
<213> ORGANISM: Artificial Sequence
<220> FEATURE:
<223> OTHER INFORMATION: sequencing primer S2 molecule

<400> SEQUENCE: 3
ccatctcatc cctgcgtgtc tccgac                                          26

<210> SEQ ID NO 4
<211> LENGTH: 92
<212> TYPE: DNA
<213> ORGANISM: Artificial Sequence
<220> FEATURE:
<223> OTHER INFORMATION: DNA fragment to be tested
<220> FEATURE:
<221> NAME/KEY: misc_feature
<222> LOCATION: (31)..(40)
<223> OTHER INFORMATION: n is a, t, c or g
<220> FEATURE:
<221> NAME/KEY: misc_feature
<222> LOCATION: (41)..(70)
<223> OTHER INFORMATION: n is a, c, g, t or no nucleotide

<400> SEQUENCE: 4
```

```
ccatctcatc cctgcgtgtc tccgactcag nnnnnnnnnn nnnnnnnnnn nnnnnnnnnn      60
nnnnnnnnnn tcaccgactg cccatagaga gg                                   92
```